United States Patent [19]
Gavrias

[11] Patent Number: 6,090,581
[45] Date of Patent: Jul. 18, 2000

[54] *ASPERGILLUS FUMIGATUS* AUXOTROPHS, AUXOTROPHIC MARKERS AND POLYNUCLEOTIDES ENCODING SAME

[75] Inventor: Vicky Gavrias, Upton, Mass.

[73] Assignee: Millenium Pharmaceuticals, Inc., Cambridge, Mass.

[21] Appl. No.: 09/040,681

[22] Filed: Mar. 18, 1998

Related U.S. Application Data

[60] Provisional application No. 60/041,300, Mar. 18, 1997.
[51] Int. Cl.$^7$ .......................... C12P 21/06; C12N 15/00; C12N 1/20; C12N 1/14; C07H 21/02
[52] U.S. Cl. .................. 435/69.1; 435/320.1; 435/252.1; 435/6; 435/256.1; 536/23.1
[58] Field of Search ................................ 435/320.1, 69.1, 435/256.1, 325, 252.3, 6; 536/23.1, 23.7

[56] References Cited

PUBLICATIONS

D'Enfert et al. "Attenuated Virulence of Uridine–Uracil Auxotrophs of *Aspergillus fumigatus*" Infection and Immunity, Oct. 1996, vol. 64, No. 10, pp. 4401–4405, see entire document.

Sikorski et al. "A system of shuttle vectors and yeast host strains designed for efficient manipulation of DNA in *Saccharomyces cerevisiae*" Genetics, May 1989, vol. 122, pp. 19–27, see entire document.

Sikorski et al. "In vitro Mutagenesis Plasmid Shuffling: From Cloned Gene to Mutant Yeast" Methods in Enzymology, 1991, vol. 194, pp. 302–318, see entire document.

*Primary Examiner*—Rebecca E. Prouty
*Assistant Examiner*—M. Monshipouri
*Attorney, Agent, or Firm*—Elliot M. Olstein; Alan J. Grant

[57] ABSTRACT

This invention relates to newly identified auxotrophs, polynucleotides, polypeptides encoded by such polynucleotides, the use of such polynucleotides and polypeptides, as well as the production and isolation of such polynucleotides and polypeptides. More particularly, the polynucleotides and polypeptides of the present invention have been putatively identified as being very important to the growth and/or reproduction of *Aspergillus fumigatus*.

8 Claims, 10 Drawing Sheets

Figure 1A

```
1/1                                                                                    31/11
ATG TCT CTC CCC GCA CGA ACA GCG ACC GTC TCG CGG GTG ACC AAC GAG ACC AAG ATC CAG
Met ser leu pro ala arg thr ala thr val ser arg val thr asn glu thr lys ile gln
61/21                                                     91/31
GTG TCT CTC TCT CTC GAC GGC GGC GTC CTC CCT CCA TAT GAG CCG TCA GAT CAT TTC CCT
val ser leu ser leu asp gly gly val leu pro pro tyr glu pro ser asp his phe pro
121/41                                     151/51
GCT CCT GAA GAC CCG AAG GAG GCA GAG GCC AAG CAT GGC ATC GTC CCC CCC AAA AAT
ala pro glu asp pro lys glu ala glu ala lys his gly ile val pro pro lys asn
181/61                                                     211/71
GCC GCC CAT GCG ACC CAG TTC ACA CCG ACC CAG ATC ACC GTA AGC ACG GGG ATC GGA
ala ala his ala thr gln phe thr pro thr gln ile thr val ser thr gly ile gly
241/81                                     271/91
TTT CTG GAT CAC ATG CTG CAT GCT CTC GCC AAA CAC AAG CTA TCT GGG TGG AGT TTA GCC ATC AGA
phe leu asp his met leu his ala leu ala lys his ser gly trp ser leu ala ile arg
301/101                                                     331/111
GCC AAG GGA GAT CTG TAC ATT GAC GAC CAC CAC ACC GAA GAT ACC TTC CTT GCG CTC
ala lys gly asp leu tyr ile asp asp his his thr glu asp thr phe leu ala leu
361/121                                     391/131
GGT ACC GCC TTT ACC AAA GCT CTA GGC CAA TCT CTT GCA CGA TTT GGA CGC GGC
gly thr ala phe thr lys ala leu gly arg gln ser leu ala arg phe gly arg gly
```

Figure 1B

```
421/141
GAC GCT CCA CTC GAC GAG GCT CTC TCC TGG ATC GAC CTC TCC AGC CGT CCC TGG
asp ala pro leu asp glu ala leu ser trp ile asp leu ser ser arg pro trp
481/161                                      451/151
GCC GTG ATC AAC CTG GGC TTC AAG CGG GAG ATC GGA GAC CTG AGC ACC GAG ATG ATC
ala val ile asn leu gly phe lys arg glu ile gly asp leu ser thr glu met ile
541/181                                      511/171
ACT CAT GGA CTG CAC AGC TTC GCG CAG GCT GAT GTA ACG CTG CAT GTT GGC TGC ACA
thr his gly leu his ser phe ala gln ala asp val thr leu his val gly cys thr
601/201                                      571/191
TAC GGA GAT AAC GAC CAC CGT GCA GAG AGT GCG TTC AAG GCG CTG GCC GTA GCT ATC
tyr gly asp asn asp his arg ala glu ser ala phe lys ala leu ala val ala ile
661/221                                      631/211
CGC ACT GCC TGT ACC AGA AGG GTG GCT GGC GAA GTT GGA GCG GGA GAT GTG GTT AGT ACA
arg thr ala cys thr arg arg val ala gly glu val gly ala gly asp val val ser thr
721/241                                      691/231
AAG GGA GTG CTG
lys gly val leu
```

Figure 2A

```
1/1                                                              31/11
ATG TGG AAC TCT CCA AAG GTG GGG GTC CTC GGT CAG GGT GGA CGA ATG CTT GTT
Met trp asn ser pro lys val gly val leu gly gln gly gly arg met leu val
61/21                                                            91/31
GAG TCG GCG AAC CGA CTT AAT ATC CAG GTC AAT GTT CTG GAC GCC GGT AAC GCC CCT GCG
glu ser ala asn arg leu asn ile gln val asn val leu asp ala gly asn ala pro ala
121/41                                                           151/51
AAA CAA ATT AGC GCC CAC GAC GGC CAT GTG ACT GGC TCA TTC AAG GAT CGT GAA GCT GTG
lys gln ile ser ala his asp gly his val thr gly ser phe lys asp arg glu ala val
181/61                                                           211/71
CGG ACG TTG GCG AGG ACC TGC GAC GTT GTG ACG GCC GAG CAT GTT GAT ACA TAC
arg thr leu ala arg thr cys asp val val thr ala glu his val asp thr tyr
241/81                                                           271/91
GCT CTT GAG GAG ATC TCC GCG GAG GTC AAG GTT GAG CCC AGC TGG CAA GCG ATC CGA ACA
ala leu glu glu ile ser ala glu val lys val glu pro ser trp gln ala ile arg thr
301/101                                                          331/111
ATC CAG AAC AAG TTC AAT CAG AAG GAA CAC CTT CGG AAA TAT GGC TTG TAT GGC ATG GCG GAG
ile gln asn lys phe asn gln lys glu his leu arg lys tyr gly ile pro met ala glu
361/121                                                          391/131
CAC CGG GAG CTG CTT GAG AAC ACG CCG GCT CTC GCC GAA CAG ATC GGC GAA CAG CTT GGG
his arg glu leu leu glu asn thr pro ala leu ala glu gln ile gly glu gln leu gly
```

Figure 2B

```
421/141
TAT CCC TTG ATG CTC AAG TCG AAG ACG ATG GCC TAC GAC GGA CGG GGA AAC TTC CGT GTC
tyr pro leu met leu lys ser lys thr met ala tyr asp gly arg gly asn phe arg val
481/161                                    451/151
                                                           511/171
AAT TCC AAG GAC GAT ATC CCC GAA GCG CTT GAA GCG CTC AAG GAC CGG CCA TTG TAC GCT
asn ser lys asp asp ile pro glu ala leu glu ala leu lys asp arg pro leu tyr ala
541/181
                                                           571/191
GAG AAA TGG GCC TAC TTC AAG ATG GAA GTA ATG GCC GTA ATG GTT GTG AAA ACC AAG GAC GCG
glu lys trp ala tyr phe lys met glu val met ala val met val lys thr lys asp ala
601/201
                                                           631/211
GTC CTC TCA TAC CCC ACA GTC GAG ACA GTA CAA GAA GAT TCG ATA TGC AAG CTC GTC TAC
val leu ser tyr pro thr val glu thr val gln glu asp ser ile cys lys leu val tyr
661/221
                                                           691/231
GCA CCT GCC CGC AAT GTC TCC GAC GCC ATC AAC CAG AAA GCC CAG GAG CTA GCC CGC AAG
ala pro ala arg asn val ser asp ala ile asn gln lys ala gln glu leu ala arg lys
721/241
                                                           751/251
GCT GTC GCA GCC TTT GAC GGC AAG GGT GCT TTC GGT GTG GAG ATG TTC CTT CTC GAG GAC
ala val ala ala phe asp gly lys gly ala phe gly val glu met phe leu leu glu asp
781/261
                                                           811/271
GAC AGC ATC ATG CTG TGC GAA ATT GCC CGC ATC CAC AAC TCG GGC CAC TAC ACA ATT
asp ser ile met leu cys glu ile ala ser arg ile his asn ser gly his tyr thr ile
```

Figure 2C

```
841/281
GAA GGT TGT ACC CTG TCC CAA TTT GAC GCC CAC CTA CGT GCC ATT CTC GAC CTC CCC ATT
glu gly cys thr leu ser gln phe asp ala his leu arg ala ile leu asp leu pro ile
901/301                              871/291
CCC CCT CAG AGC CTC GAA ATC CGC CAA CCG TCC ATC ATG CTC AAC ATC ATT GGC GGC GCC
pro pro gln ser leu glu ile arg gln pro ser ile met leu asn ile ile gly gly ala
                                     931/311
GCC CCA GAC ACC CAC CTG AAA GCC GCT CTC TCC ATC CCC AAC GCC AGC ATT
ala pro asp thr his leu lys ala ala leu ser ile pro asn ala ser ile
961/331
1021/341
CAC CTC TAC AGC AAG GGC GCC GCC AAG CGC AAG ATG GGC CAC GTC ACC GTT ACC
his leu tyr ser lys gly ala ala lys pro gly arg lys met gly his val thr val thr
1081/361                             1051/351
GCG TCC ACG ATG CAC GAA GCC GAG AAA TAC ATC CAG CCC CTG ATC GAC GTT GTT GAC GAG
ala ser thr met his glu ala glu lys tyr ile gln pro leu ile asp val val asp glu
1141/381                             1111/371
ATC CGC TCG AAG CGC AGC AGC GAC ATC AAG ACA CAG CCC GTC AAG TCC GGC CCG AAG CCC
ile arg ser lys arg ser ser asp ile lys thr gln pro val lys ser gly pro lys pro
1201/401                             1171/391
GCC CCC ACC GTT GCT GTG ATG ATG GGC TCC GAT AGC GAC CTC AAG ACA CTC GTT CCG GGC
ala pro thr val ala val met met gly ser asp ser asp leu lys thr leu val pro gly
                                     1231/411
```

Figure 2D

```
1261/421
CTG AAA CTC CTC CGT GAC TAC TTC GGC ATC GAG CCC GCC GTC GAC ATC ACC TCC GCC CAT
leu lys leu leu arg asp tyr phe gly ile glu pro ala val asp ile thr ser ala his
1321/441                                                              1351/451
CGC ACC CCA ACG TTC ATG GCC GAG TAC TCA GCC AGC GCA GCC CGC GGC ATT AAG GTC
arg thr pro thr phe met ala glu tyr ser ala ser ala ala arg gly ile lys val
1381/461                                        1411/471
ATT ATC GCC GCT GCG GCG GGC GCC CAT CTC CCT GGG ATG GCT GCC GCA CAC ACC GTC
ile ile ala ala ala gly gly ala his leu pro gly met ala ala ala his thr val
1441/481                                1471/491
CTG CCC GTC ATC GGC GTA CCG GTC AAG GGC GTG GAC AGC CTG TAC
leu pro val ile gly val pro val lys gly ser ser leu asp gly val asp ser leu tyr
1501/501                                                        1531/511
AGC ATC GTC CAG ATG CCT AGA GGT GTT CCC GTC GCG ACG GTA GGA ATC AAC AAC AGC ATC
ser ile val gln met pro arg gly val pro val ala thr val gly ile asn asn ser ile
1561/521                                                        1591/531
AAC GCT GCC CTC CTG GCA GCT CGT ATC CTT GGC ACA TTC GAC CCG GCT ATC CAG CGT AAG
asn ala ala leu leu ala ala arg ile leu gly thr phe asp pro ala ile gln arg lys
1621/541                                                        1651/551
GTG GAG GCG TAT GCC GAG CAG GCT AGA CAC GCG CAG GCT AAC ATG GAG AAC ATG GAG AAC ATG GAG TTG AAG GGG ACC AAG ATG
val glu ala tyr ala glu gln ala arg his ala arg gln ala asn met glu leu lys gly thr lys met
1681/561                                                        1711/571
CAG GAA CTC GGA TGG GAA AAG TAC TTT GAA CAG ATG
gln glu leu gly trp glu lys tyr phe glu gln met
```

Figure 3A

```
1/1                                                          31/11
ATG CCG TCA TAT AAC ATT GTC GTT TTC GCT GGG GAC CAC TGT GGT CCG GAG GTG ACC GCT
Met pro ser tyr asn ile val val phe ala gly asp his cys gly pro glu val thr ala
61/21                                                        91/31
GAG GCA ATC AAG GTC CTG CGC GTC ATC GAG ATC GAG AAG TGC CGT GAC GAT GCT ACC TTC AAC CTC
glu ala ile lys val leu arg val ile glu lys cys arg asp asp ala thr phe asn leu
121/41                                                       151/51
CAG GAT CAA TTG CTC GGT GGT GCA TCG ATC GAT GCT ACC GGA TCT CCC CTT ACC GAC GAA
gln asp gln leu leu gly gly ala ser ile asp ala thr gly ser pro leu thr asp glu
181/61                                                       211/71
GCT CTT AAC GCC GCA AAG AAC GCC GAT GCC GTT CTC CTC GGT GCC ATT GGC ATA GGT CCC AAA
ala leu asn ala ala lys asn ala asp ala val leu leu gly ala ile gly gly pro lys
241/81                                                       271/91
TGG GGC ACT GGC GCC GTC CGC CCC GAA CAG GGC CTC CGT CTG CGC AAG GAG ATG GGC
trp gly thr gly ala val arg pro glu gln gly leu arg leu arg lys glu met gly
301/101                                                      331/111
ACA TTC GGT AAC CTC CGC CCC TGC AAC TTC GCC GCC CCG TCG CTG GTC GAC GGC TCC CCT
thr phe gly asn leu arg pro cys asn phe ala ala pro ser leu val asp gly ser pro
```

Figure 3B

```
361/121
CTC CGC CCC GAA GTC TGC CGC GGC GTC GAC ATT ATC CGC GAA CTG ACC GGT GGC
leu arg pro glu val cys arg gly val asp ile ile arg glu leu thr gly gly
421/141                            391/131
ATC TAC TTC GGC GAC CGC AAG GAG GAC GGC AGC GGC TTC GCC ATG GAC ACG CCG
ile tyr phe gly asp arg lys glu asp gly ser gly phe ala met asp thr pro
481/161                            451/151
TAC TCC CGC GCG GAG ATC GAG CGC ATC ACC CGC CTT GCG GCC CAC CTC GCT CTG CAG CAC
tyr ser arg ala glu ile glu arg ile thr arg leu ala ala his leu ala leu gln his
541/181                            511/171
AAC CCC CCT CTT CCC GTG TGG AGC TTG GAC GCC AAG GTC CTC GCG ACG AGC CGG CTG
asn pro pro leu pro val trp ser leu asp ala lys val leu ala thr ser arg leu
601/201                            571/191
TGG CGG AAG ACC GTG ACG GAG GTC ATG GCC AAG GAG TTC CCC CAG CTC AAG GTG GAG CAC
trp arg lys thr val thr glu val met ala lys glu phe pro gln leu lys val glu his
661/221                            631/211
CAG CTC ATT GAC TCC GCG GCC ATG ATC ATG GTC AAG GAG CCT AGA AAG CTT AAC GGT ATT
gln leu ile asp ser ala ala met ile met val lys glu pro arg lys leu asn gly ile
                                   691/231
```

Figure 3C

721/241
GTT GTC ACT AGC AAC CTG TTC GGT GAC ATC AGT GAT GAA GCC AGC GTT ATC CCT GGT
val val thr ser asn leu phe gly asp ile ser asp glu ala ser val ile pro gly
781/261
                                        751/251
TCT CTG GGA CTC TTG CCC AGC GCA AGC TTG AGC ATT CCT GAC GGA AAG ACC AAG GTC
ser leu gly leu leu pro ser ala ser leu ser gly ile pro asp gly lys thr lys val
841/281                                 811/271
AAT GGT ATC TAT GAG CCT ATT CAC GGT TCT GCC CCT GAC ATT GCC AAG GGC ATC GTT
asn gly ile tyr glu pro ile his gly ser ala pro asp ile ala gly lys gly ile val
901/301                                 871/291
AAC CCC GTC GCC GCC ATT CTC TCT GTC GCC ATG ATG ATG CAG TAC TCC CTG AAC CGT ATG
asn pro val ala ala ile leu ser val ala met met met gln tyr ser leu asn arg met
961/321                                 931/311
GAT GAC GCC AGG GCC ATC GAG ACG GCC GTC AAT GTG CGC AAT GTG AGG AAT GTG ATC GAG GCC GGT ATC GAG GCC ACT
asp asp ala arg ala ile glu thr ala val arg asn val ile glu ala gly ile glu arg thr
1021/341                                991/331
GCC GAT ATT GGC GGC AAG TCG ACA ACT AGC GAG GTC GGT GAC GCT GTT GCT GCC GAG CTG
ala asp ile gly gly lys ser thr thr ser glu val gly asp ala val ala ala glu leu
1081/361                                1051/351
GAG AAG CTG TTG AAG CAA
glu lys leu leu lys gln

IMIDAZOLEGLYCEROL-P DEHYDRATASE

A. fumifatus hisB Knockout Construction

6,090,581

ASPERGILLUS FUMIGATUS AUXOTROPHS, AUXOTROPHIC MARKERS AND POLYNUCLEOTIDES ENCODING SAME

This application claims the benefit of Provisional Application Ser. No. 60/041,300, filed Mar. 18, 1997.

This invention relates to newly identified auxotrophs, polynucleotides, polypeptides encoded by such polynucleotides, the use of such polynucleotides and polypeptides, as well as the production and isolation of such polynucleotides and polypeptides. More particularly, the polynucleotides and polypeptides of the present invention have been putatively identified as being very important to the growth and/or reproduction of *Aspergillus fumigatus*.

Generally, such proteins are of such importance to the growth and/or reproduction of *Aspergillus fumigatus* that modifications to the protein or to the polynucleotide encoding same, blocking the expression or activity of the protein, or deleting or disabling the polynucleotide encoding the protein will have an significant and clearly observable effect on either the growth or reproduction of the organism in vitro. In fact, absent a supplemented media having a particular substance that would have resulted from the synthesis pathway in which the protein functions, the *Aspergillus fumigatus* auxotrophs will die.

In accordance with one aspect of the present invention there are provided auxotrophic microbes of the *Aspergillus fumigatus* type, which are incapable of growth and reproduction in vitro in the absence of a media supplemented by at least one chemical compound that is not required for a non-auxotrophic microbe of the *Aspergillus fumigatus* type.

In accordance with another aspect of the present invention, there are provided novel proteins, as well as active fragments, analogs and derivatives thereof.

In accordance with another aspect of the present invention, there are provided isolated nucleic acid molecules encoding the proteins of the present invention including mRNAs, cDNAs, genomic DNAs as well as active analogs and fragments of such proteins.

In accordance with another aspect of the present invention there are provided strains of auxotrophic *Aspergillus fumigatus* microbe which have the ATCC Deposit Nos. AFH153 209347, AFLEU2 209348, AFADE2 209349.

In accordance with another aspect of the present invention there are provided isolated nucleic acid molecules encoding mature polypeptides expressed by the DNA contained in ATCC Deposit Nos. AFH153 209347AFLEU2 209348, and AFADE2 209349.

In accordance with yet a further aspect of the present invention, there is provided a process for producing such polypeptides by recombinant techniques comprising culturing recombinant prokaryotic and/or eukaryotic host cells, containing a nucleic acid sequence of the present invention, under conditions promoting expression of said proteins and subsequent recovery of said proteins.

In accordance with yet a further aspect of the present invention, there is provided a process for utilizing such proteins to produce antibodies specific for such proteins to permit analyzing a vector or host cell for the presence of the protein, which is heterologous to said vector or host cell. Thus, the protein is useful as a heterologous marker wherein the polynucleotide sequence encoding the protein is part of a construct inserted into a vector or host wherein such protein would be heterologous.

In accordance with a still further aspect of the invention another process utilizes the polynucleotides to assay for compounds which bind said polynucleotides and would thus block expression of any products from said polynucleotides.

In another aspect polynucleotides of the invention may be employed as a tool for studying *Aspergillus fumagatus* to ascertain various genes thereof, particularly other essential genes. One such process is useful for analyzing for the functionality of an unknown function cDNA from an *Aspergillus fumigatus* cDNA library comprising obtaining an auxotrophic strain of *Aspergillus fumigatus*, obtaining a polynucleotide construct comprising (i) a polynucleotide sequence capable of removing the auxotrophic property and (ii) at least one portion of the unknown function cDNA polynucleotide sequence. which is not the complete cDNA sequence from the cDNA library, and inserting said construct into said auxotrophic strain. Preferably, such a process involves an auxotroph that requires either histidine, adenylic acid, or leucine to grow and reproduce. A further preferred process, comprises assaying the auxotrophic strain for growth and reproduction in a media which lacks, histidine, adenylic acid, or leucine to confirm insertion of the construct. An ever further preferred process also comprises assaying the strain with the insertion for a lost property, which would have resulted from the unknown cDNA corresponding to the cDNA of the cDNA library.

*Aspergillus fumagatus* are microbe which are useful as host cells for the expression of heterologous polynucleotide sequences and for production of heterologous proteins. It would be helpful in such an environment to map more or all of the genes in this microbe in order to enhance its use as a host cell for expression or heterologous polynucleotide sequences and for production of heterologous proteins. Auxotrophs are useful in that they need a specific supplement in their media or they don't grow or reproduce, and in fact may die. Thus, advantageously, a construct is made which comprises either the head or tail portion (preferably at lest 250 base pairs in length) of the polynucleotide sequence that will cure (remove) the auxotrophic property ligated to the heterologous gene which is in turn ligated to the full polynucleotide sequence which will remove the auxotrophic property. Preferably, the construct may comprise a promoter sequence or a secretion coding sequence for the heterologous gene. Therefore, if a heterologous polynucleotide construct is inserted into the auxotroph which includes the gene encoding a protein or polypeptide (preferably according to this invention) which will eliminate the need for the supplement in the media, the auxotrophs can be conveniently screened for the successful insertion of the construct.

After attempts to insert the construct by homologous recombination (cross-over) in the auxotroph, the potential transformants are plated on supplemented media to culture colonies from a single isolated cell. Cells from a particular colony can then be plated on a media which lacks the supplement required by the starting auxotroph, species where insertion has been successful will grow on the media lacking that supplement, but species lacking the insert will fail to grow or reproduce and in fact may die. Accordingly, auxotrophs are useful tools to screen for successful insertion of heterologous genes which are part of a construct that removes the auxotrophic property of the auxotroph.

Such auxotrophs and the polynucleotides which encode for a protein which will remove a particular auxotrophic property of the auxotroph are also useful tools in the study of the genus or species of microbe from which the auxotroph is obtained. A vector containing a cDNA of unknown function from a cDNA library for the microbe may be utilized to form a construct having only a portion of the cDNA and including the known polynucleotide encoding the known protein which will eliminate the auxotrophic property of the auxotroph. The active gene corresponding to the cDNA from the library is disabled by successful insertion of the construct. For example, the culture is screened for successful insertion of the construct as discussed above, in a media which is fully supplemented except for the supplement required by the starting auxotroph. Species having the successful insertion, may then be studied to obtain the property of the disabled gene corresponding to the cDNA. For example, supplements may be individually omitted from the growth media until an effect is observed such as diminished growth or death, and the area of functionally of the gene corresponding to the cDNA is thus identified.

Accordingly, a process to determine the function of unknown genes within *Aspergillus fumigatus* utilizing the polynucleotides and/or proteins of the present invention is also an important and useful procedure made possible by the present invention.

There are other applications for the proteins and polynucleotides of the present invention in various industries which may utilize such microbe, such as in the fermentation industry. Since such proteins and/or polynucleotides have been found to be significantly essential to the growth and/or reproduction of *Aspergillus fumigatus* they may be useful to determine agonist which may enhance the growth and/or reproduction of such microbe in such fermentation processes. Moreover, the expression products of the polynucleotides according to the invention may be useful to enhance the growth of such microbe, e.g., multiple copies of the present gene in *Aspergillus fumigatus* may prove to enhance its growth or reproductive rates.

In accordance with yet a further aspect of the present invention, there are also provided nucleic acid probes comprising nucleic acid molecules of sufficient length to specifically hybridize to a nucleic acid sequence of the present invention.

In accordance with yet a further aspect of the present invention, there is provided a process for utilizing such proteins, or polynucleotides encoding such proteins, for purposes related to scientific research, for example, to generate probes for identifying similar sequences which might encode similar proteins from other organisms by using certain regions, i.e., conserved sequence regions, of the nucleotide sequence.

These and other aspects of the present invention should be apparent to those skilled in the art from the teachings herein.

BRIEF DESCRIPTION OF THE DRAWINGS

The following drawings are illustrative of an embodiment of the invention and are not meant to limit the scope of the invention as encompassed by the claims.

FIGS. 1–4

FIG. 1 illustrates a nucleotide sequence from a *Aspergillus fumagatus* cDNA (SEQ ID NO:1) encoding and the deduced amino acid sequence (SEQ ID NO:2) therefor. The omission of such polynucleotide from *Aspergillus fumagatus* results in an auxotrophic species that require a growth media supplemented with the amino acid histicine. The top line of each set of rows is the polynucleotide sequence, the second line contains the three-letter codes representing the deduced amino acid sequence encoded by the polynucleotide.

FIG. 2 illustrates a nucleotide sequence from a *Aspergillus fumagatus* cDNA (SEQ ID NO:3) encoding and the deduced amino acid sequence (SEQ ID NO:4) therefor. The omission of such polynucleotide from *Aspergillus fumagatus* results in an auxotrophic species that require a growth media supplemented with adenylic acid. The top line of each set of rows is the polynucleotide sequence, the second line contains the three-letter codes representing the deduced amino acid sequence encoded by the polynucleotide.

FIG. 3 illustrates a nucleotide sequence from a *Aspergillus fumagatus* cDNA (SEQ ID NO:5) encoding and the deduced amino acid sequence (SEQ ID NO:6) therefor. The omission of such polynucleotide from *Aspergillus fumagatus* results in an auxotrophic species that require a growth media supplemented with the amino acid leucine. The top line of each set of rows is the polynucleotide sequence, the second line contains the three-letter codes representing the deduced amino acid sequence encoded by the polynucleotide.

FIG. 4 illustrates the structure of a hisB knockout construct which may be utilized to produce an auxotroph which requires a medium supplemented with the amino acid histidine. In this illustration a construct is made which corresponds to the portions of the head and tail of the polynucleotide according to nucleotide sequence SEQ ID NO:1 from *Aspergillus fumigatus* having sandwiched in between a gene for hygB. An hygB insert having a BamHI/SalI fragment is shown. Inverse digestion is utilized to cut out the middle portion of the polynucleotide according to SEQ ID NO:1 and the hygB fragment is inserted to form the construct.

Figure 4:
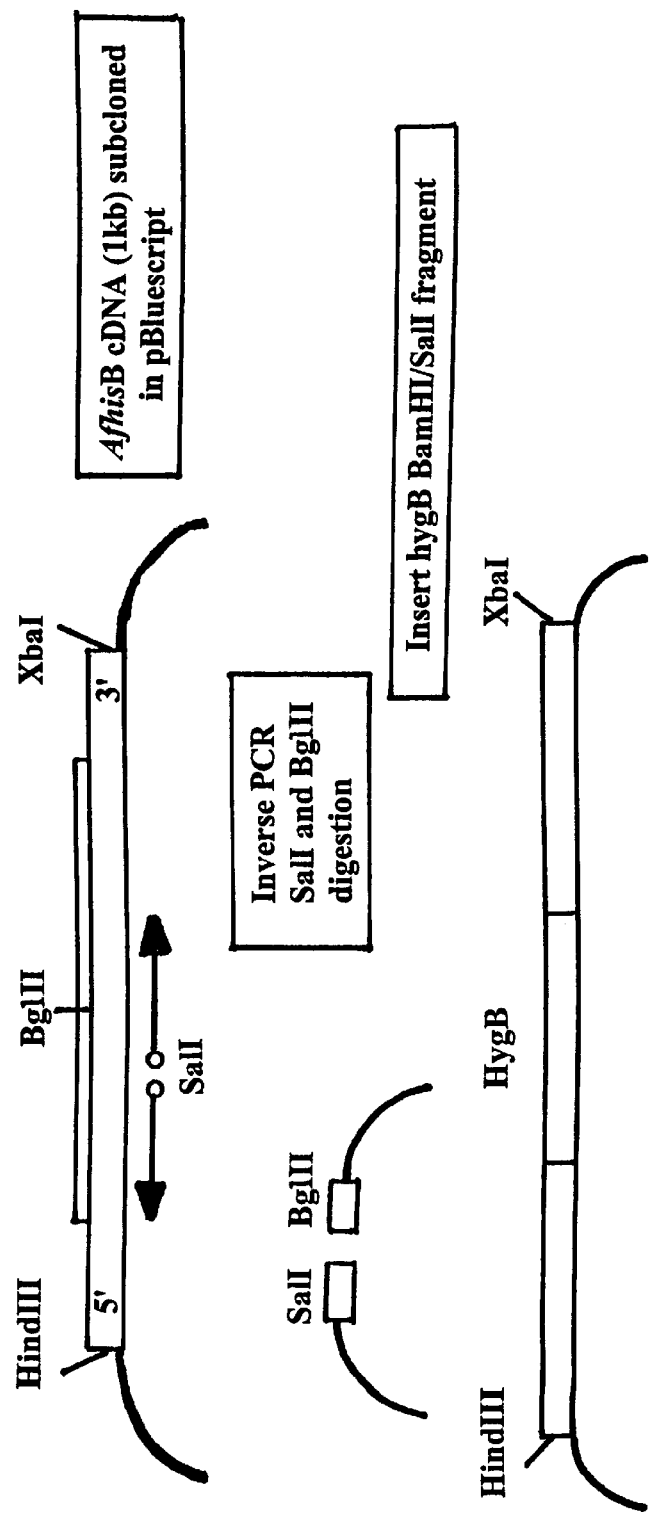

*Aspergillus fumigatus* was transformed with the construct described in FIG. 4 to permit cross-over replacement of the gene corresponding to SEQ ID NO:1 with the construct in a medium supplemented with amino acid histiding. In such cross-over replacement the construct substitutes itself for the polynucleotide sequence according to SEQ ID NO:1 which is then eliminated by the cell. The cells were screened using screening procedures to assay members of pure colonies for the auxotrophic property of requiring a medium supplemented by the amino acid histidine. Of 175 colonies potential transformants screened in medium lacking the amino acid histidine, 20 transformant species were identified as auxotrophs of *Aspergillus fumigatus* that require histidine for growth.

DEFINITIONS

In order to facilitate understanding of the following description and examples which follow certain frequently occurring methods and/or terms will be described.

The term "auxotroph" refers to a species of a cell type, whether naturally occurring or is produced by other means which requires at least one supplement in its growth media in order to grow and reproduce, as contrasted to a species which does not require such a supplement for growth and reproduction.

The term "construct" refers to a polynucleotide segment adapted to insertion into a longer polynucleotide via a ligation procedure or by cross-over replacement of a portion of the longer chain polynucleotide.

The term "cross-over replacement" refers to the replacement of a portion of a polynucleotide chain with a construct by alignment of the construct with a portion of a polynucleotide chain in a cell such that the portion is replaced with the construct and the original polynucleotide portion is eliminated. Such cross-over replacement is most likely to occur during a reproduction phase of the cell.

The term "gene" means the segment of DNA involved in producing a polypeptide chain; it includes regions preceding and following the coding region (leader and trailer) as well as intervening sequences (introns) between individual coding segments (exons).

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein.

"Recombinant" proteins refer to proteins produced by recombinant DNA techniques; i.e., produced from cells transformed by an exogenous DNA construct encoding the desired protein. "Synthetic" proteins are those prepared by chemical synthesis.

A DNA "coding sequence of" or a "nucleotide sequence encoding" a particular protein, is a DNA sequence which is transcribed and translated into a protein when placed under the control of appropriate regulatory sequences.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel et al., *Nucleic Acids Res.,* 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in Sambrook and Maniatis, Molecular Cloning: A Laboratory Manual, Cold Spring Harbor Laboratory, 1989.

SUMMARY OF THE INVENTION

In accordance with an aspect of the invention there are provided auxotrophic microbes of the *Aspergillus fumigatus* type, which either lack or have disabled one or more of the genes corresponding to a polynucleotide sequence selected from SEQ ID NO:1, 3, or 5, respectively, requiring histidine, adenylic acid, or leucine for growth and reproduction. The deposited auxotrophs are deposited with the American Type Culture Collection, 10801 University Blvd., Manassas, Va. 20110-2209, the deposited materials are assigned ATCC Deposit Nos. AFH153 209347, AFLEU2 209348, and AFADE2 209349 (corresponding to FIGS. 1–3, respectively).

In accordance with an aspect of the present invention, there are provided isolated nucleic acids (polynucleotides) from *Aspergillus fumigatus* (SEQ ID NOS: 1, 3 and 5) which encode the mature protein having the continuous deduced amino acid sequence shown in FIGS. 1–3, respectively (SEQ ID NOS:2, 4 and 6, respectively).

In accordance with another aspect of the present invention, there is provided isolated polynucleotides encoding the proteins of the present invention. The deposited material is a genomic clone comprising DNA encoding a protein of the present invention, in a plasmid DNA vector form. As deposited with the American Type Culture Collection, 10801 University Blvd., Manassas, Va. 20110-2209, the deposited materials are assigned ATCC Deposit Nos. AFH153 209347, AFLEU2 209348, and AFADE2 209349 (corresponding to FIGS. 1–3, respectively).

The deposits have been made under the terms of the Budapest Treaty on the International Recognition of the Deposit of Micro-organisms for Purposes of Patent Procedure. The clones will be irrevocably (without restriction or condition except as permitted for enforcement of a patent) released to the public upon the issuance of a patent. The deposits are provided merely as a convenience to those of skill in the art and is not an admission that any deposit would be required under 35 U.S.C. §112. The sequence of the polynucleotide contained in the respective deposited materials, as well as the amino acid sequences of the polypeptide encoded thereby, are controlling in the event of any conflict with any description of sequences herein. A license may be required to make, use or sell the deposited material, and no such license is hereby granted.

DETAILED DESCRIPTION OF THE INVENTION

The polynucleotides of this invention coding for the proteins of this invention were originally recovered from a genomic gene library derived from *Aspergillus fumigatus.*

One means for isolating the nucleic acid molecules encoding the proteins of the present invention is to probe a *Aspergillus fumigatus* gene library with a natural or artificially designed probe using art recognized procedures (see, for example: Current Protocols in Molecular Biology, Ausubel F. M. et al. (EDS.) Green Publishing Company Assoc. and John Wiley Interscience, New York, 1989, 1992). It is appreciated by one skilled in the art that the polynucleotides of SEQ ID NOS:1, 3 and 5, or fragments thereof (comprising at least 12 contiguous nucleotides), are particularly useful probes. Other particularly useful probes for this purpose are hybridizable fragments of the sequences of SEQ ID NOS:1, 3 and 5 (i.e., comprising at least 12 contiguous nucleotides).

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acids is first prehybridized for 30 minutes at 45° C. in a solution consisting of 0.9 M NaCl, 50 mM NaH$_2$PO$_4$, pH 7.0, 5.0 mM Na$_2$EDTA, 0.5% SDS, 10× Denhardt's, and 0.5 mg/mL polyriboadenylic acid. Approximately 2×10$^7$ cpm (specific activity 4–9×10$^8$ cpm/ug) of $^{32}$P end-labeled oligonucleotide probe are then added to the solution. After 12–16 hours of incubation, the membrane is washed for 30 minutes at room temperature in 1× SET (150 mM NaCl, 20 mM Tris hydrochloride, pH 7.8, 1 mM Na$_2$EDTA) containing 0.5% SDS, followed by a 30 minute wash in fresh 1× SET at Tm less 10° C. for the oligonucleotide probe. The membrane is then exposed to auto-radiographic film for detection of hybridization signals.

Stringent conditions means hybridization will occur only if there is at least 90% identity, preferably at least 95% identity and most preferably at least 97% identity between the sequences. Further, it is understood that a section of a 100 bps sequence that is 95 bps in length has 95% identity with the 1090 bps sequence from which it is obtained. See J. Sambrook et al., *Molecular Cloning, A Laboratory Manual*, 2d Ed., Cold Spring Harbor Laboratory (1989) which is hereby incorporated by reference in its entirety. Also, it is understood that a fragment of a 100 bps sequence that is 95 bps in length has 95% identity with the 100 bps sequence from which it is obtained.

As used herein, a first DNA (RNA) sequence is at least 70% and preferably at least 80% identical to another DNA (RNA) sequence if there is at least 70% and preferably at least a 80% or 90% identity, respectively, between the bases of the first sequence and the bases of the another sequence, when properly aligned with each other, for example when aligned by BLASTN.

The present invention relates to polynucleotides which differ from the reference polynucleotide in a manner such that the change or changes is/are silent change, in that the amino acid sequence encoded by the polynucleotide remains the same. The present invention also relates to nucleotide changes which result in amino acid substitutions, additions, deletions, fusions and truncations in the polypeptide encoded by the reference polynucleotide. In a preferred aspect of the invention these polypeptides retain the same biological action as the polypeptide encoded by the reference polynucleotide.

The polynucleotides of the present invention may be in the form of RNA or DNA which DNA includes cDNA, genomic DNA, and synthetic DNA. The DNA may be double-stranded or single-stranded, and if single stranded may be the coding strand or non-coding (anti-sense) strand. The coding sequences which encodes the mature proteins may be identical to the coding sequences shown in FIGS. 1–3, (SEQ ID NOS:1, 3 and 5, respectively) or may be a different coding sequence which coding sequence, as a result of the redundancy or degeneracy of the genetic code, encodes the same mature proteins as does the DNA of FIGS. 1–3, (SEQ ID NOS:1, 3 and 5, respectively).

The polynucleotides which encode each of the mature proteins (SEQ ID NOS:2, 4 and 6, respectively) may include, but each is not limited to: only the coding sequence for the mature protein; the coding sequence for the mature protein and additional coding sequence such as a leader sequence or a proprotein sequence; the coding sequence for the mature protein (and optionally additional coding sequence) and non-coding sequence, such as introns or non-coding sequence 5' and/or 3' of the coding sequence for the mature protein.

Thus, the term "polynucleotide encoding a protein" encompasses a polynucleotide which includes only coding sequence for the protein as well as a polynucleotide which includes additional coding and/or non-coding sequences.

The present invention further relates to variants of the hereinabove described polynucleotides which encode for fragments, analogs and derivatives of the proteins having the deduced amino acid sequences of FIGS. 1–3 (SEQ ID NOS: 2, 4 and 6, respectively). The variant of the polynucleotide may be a naturally occurring allelic variant of the polynucleotide or a non-naturally occurring variant of the polynucleotide.

Thus, the present invention includes polynucleotides encoding the same mature proteins as shown in FIGS. 1–3, as well as variants of such polynucleotides which variants encode for a fragment, derivative or analog of the proteins of FIGS. 1–3, respectively. Such nucleotide variants include deletion variants, substitution variants and addition or insertion variants.

As hereinabove indicated, the polynucleotides may have a coding sequence which is a naturally occurring allelic variant of the coding sequence shown in FIGS. 1–3. As known in the art, an allelic variant is an alternate form of a polynucleotide sequence which may have a substitution, deletion or addition of one or more nucleotides, which does not substantially alter the function of the encoded protein. Also, using directed and other evolution strategies, one may make very minor changes in DNA sequence which can result in major changes in function.

Fragments of the full length gene of the present invention may be used as hybridization probes for a cDNA or a genomic library to isolate the full length DNA and to isolate other DNAs which have a high sequence identity to the gene. Probes of this type preferably have at least 10, preferably at least 15, and even more preferably at least 30 bases and may contain, for example, at least 50 or more bases. In fact, probes of this type having at least up to 150 bases or greater may be utilized. The probe may also be used to identify a DNA clone corresponding to a full length transcript and a genomic clone or clones that contain the complete gene including regulatory and promotor regions, exons and introns. An example of a screen comprises isolating the coding region of the gene by using the known DNA sequence to synthesize an oligonucleotide probe. Labeled oligonucleotides, having a sequence complementary to that of the gene or portion of the gene sequences of the present invention are used to screen a library of genomic DNA to determine which members of the library the probe hybridizes to in a complementary sense, have an identity as described above.

It is also appreciated that such probes can be and are preferably labeled with an analytically detectable reagent to facilitate identification of the probe. Useful reagents include but are not limited to radioactivity, fluorescent dyes or proteins capable of catalyzing the formation of a detectable product. The probes are thus useful to isolate complementary copies of DNA from other sources or to screen such sources for related sequences.

The present invention further relates to polynucleotides which hybridize to the hereinabove-described sequences if there is at least 70%, preferably at least 90%, and more preferably at least 95% identity between the sequences. (As indicated above, 70% identity would include within such definition a 70 bps fragment taken from a 100 bp polynucleotide, for example.) The present invention particularly relates to polynucleotides which hybridize under stringent conditions to the hereinabove-described polynucleotides. As herein used, the term "stringent conditions"

means hybridization will occur only if there is at least 95% and preferably at least 97% identity between the sequences. The polynucleotides which hybridize to the hereinabove described polynucleotides in a preferred embodiment encode proteins which either retain substantially the same biological function or activity as the mature proteins encoded by the DNA of FIGS. 1–3, respectively. In referring to identity in the case of hybridization, as known in the art, such identity refers to complementarity of polynucleotide segments.

Alternatively, the polynucleotide may have at least 15 bases, preferably at least 30 bases, and more preferably at least 50 bases which hybridize to any part of a polynucleotide of the present invention and which has an identity thereto, as hereinabove described, and which may or may not retain activity. For example, such polynucleotides may be employed as probes for the polynucleotides of SEQ ID NOS: 1, 3 and 5, for example, for recovery of the polynucleotide or as a diagnostic probe or as a PCR primer.

Thus, the present invention is directed to polynucleotides having at least a 70% identity, preferably at least 90% identity and more preferably at least a 95% identity to a polynucleotide which encodes the polypeptides of SEQ ID NOS: 2, 4 and 6, respectively, as well as fragments thereof, which fragments have at least 15 bases, preferably at least 30 bases, more preferably at least 50 bases and most preferably fragments having up to at least 150 bases or greater, which fragments are at least 90% identical, preferably at least 95% identical and most preferably at least 97% identical to any portion of a polynucleotide of the present invention.

The present invention further relates to proteins which have the deduced amino acid sequence of FIGS. 1–3, respectively, (SEQ ID NOS: 2, 4 and 6, respectively) as well as fragments, analogs and derivatives of such proteins.

The terms "fragment," "derivative" and "analog" when referring to each of the proteins of FIGS. 1–3, respectively, (SEQ ID NO: 2, 4 and 6, respectively) generally mean a protein which retains essentially the same biological function or activity as such protein. Thus, an analog includes a proprotein which can be activated by cleavage of the proprotein portion to produce an active mature protein.

The proteins of the present invention may be a recombinant protein, a natural protein or a synthetic protein, preferably a recombinant protein.

The present invention further relates to polypeptides encoded by polynucleotides which have at least 70%, preferably at least 90%, and more preferably at least 95% identity between their polynucleotide sequence and one of the sequences according to SEQ ID NO:1, 3 or 5, respectively. (As indicated above, 70% identity would include within such definition a 70 bps fragment taken from a 100 bp polynucleotide, for example.) The present invention particularly relates to polypeptides encoded by polynucleotides which hybridize under stringent conditions to the hereinabove-described polynucleotides or their complement. As herein used, the term "stringent conditions" means hybridization will occur only if there is at least 95% and preferably at least 97% identity between the sequences. The polynucleotides which hybridize to the hereinabove described polynucleotides in a preferred embodiment encode proteins which either retain substantially the same biological function or activity as the mature proteins encoded by the DNA of FIGS. 1–3, respectively. However, polypeptides having at least 70% or greater identity as described above are useful marker proteins in their own right regardless of whether the possess the biological activity of one of the polypeptides having an amino acid sequence according to SEQ ID NO:2, 4, or 6, respectively. Such are useful in a process to produce antibodies specific for such polypeptides to permit analyzing a vector or host cell for the presence of the polypeptide, which is heterologous to that vector or host cell. Thus, the polypeptide is useful as a heterologous marker wherein the polynucleotide sequence encoding the polypeptide is part of a construct inserted into a vector or host wherein such polypeptide would be heterologous. Pure cultures of the vector or host cell could be assayed for expression of the heterologous polypeptide to indicate a successful insertion of the construct which comprised the polynucleotide sequence encoding the heterologous polypeptide. In referring to identity in the case of hybridization, as known in the art, such identity refers to complementarity of polynucleotide segments.

The fragment, derivative or analog of each of the proteins of FIGS. 1–3, respectively, (SEQ ID NOS: 2, 4 and 6, respectively) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature protein is fused with another compound, such as a compound to increase the half-life of the protein (for example, polyethylene glycol), or (iv) one in which the additional amino acids are fused to the mature protein, such as a leader or secretory sequence or a sequence which is employed for purification of the mature protein or a proprotein sequence. Such fragments, derivatives and analogs are deemed to be within the scope of those skilled in the art from the teachings herein.

The proteins and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or protein present in a living animal is not isolated, but the same polynucleotide or protein, separated from some or all of the coexisting materials in the natural system, is isolated. Such polynucleotides could be part of a vector and/or such polynucleotides or proteins could be part of a composition, and still be isolated in that such vector or composition is not part of its natural environment.

The proteins of the present invention include the respective proteins of SEQ ID NOS: 2, 4 and 6, (in particular the mature proteins) as well as proteins which have at least 70% similarity (preferably at least 70% identity) to the respective proteins of SEQ ID NOS: 2, 4 and 6 and more preferably at least 90% similarity (more preferably at least 90% identity) to the respective proteins of SEQ ID NOS: 2, 4 and 6, and still more preferably at least 95% similarity (still more preferably at least 95% identity) to the respective proteins of SEQ ID NOS: 2, 4 and 6, and also include portions of such proteins with such portion of the protein generally containing at least 30 amino acids and more preferably at least 50 amino acids and most preferably at least up to 150 amino acids, or more. Particularly, preferred portions are immunogenic portions that have very low homology to known proteins of a particular vector or host wherein the proteins would be heterologous.

As known in the art "similarity" between two proteins is determined by comparing the amino acid sequence and its conserved amino acid substitutes of one protein to the sequence of a second protein. The definition of 70% similarity would include a 70 amino acid sequence fragment of a 100 amino acid sequence, for example, or a 70 amino acid sequence obtained by sequentially or randomly deleting 30 amino acids from the 100 amino acid sequence.

The polypeptides corresponding to SEQ ID NOS:2, 4 and 6, respectively, and the polynucleotides encoding them, SEQ ID NOS:1, 3 and 5, display homology to ADE2, LEU2 and HIS3 of the yeast species *Saccromyces cervisiae*. Accordingly, such polypeptides according to the present invention would be expected to have similar biological activity to their respective *Saccromyces cervisiae* protein homolog.

A variant, i.e. a "fragment", "analog" or "derivative" polypeptide, and reference polypeptide may differ in amino acid sequence by one or more substitutions, additions, deletions, fusions and truncations, which may be present in any combination.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Most highly preferred are variants which retain the same biological function and activity as the reference polypeptide from which it varies.

Fragments or portions of the proteins of the present invention may be employed for producing the corresponding full-length protein by peptide synthesis; therefore, the fragments may be employed as intermediates for producing the full-length proteins. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of proteins of the invention by recombinant techniques.

Host cells are genetically engineered (transduced or transformed or transfected) with the vectors of this invention which may be, for example, a cloning vector such as an expression vector. The vector may be, for example, in the form of a plasmid, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing proteins by recombinant techniques. Thus, for example, the polynucleotide may be included in any one of a variety of expression vectors for expressing a protein. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Bacillus subtilis*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBluescript II KS, ptrc99a, pKK223-3, pDR540, pRIT2T (Pharmacia); Eukaryotic: pXT1, pSG5 (Stratagene) pSVK3, pBPV, pMSG, pSVL SV40 (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., *Basic Methods in Molecular Biology*, (1986)).

The constructs in host cells can be used in a conventional manner to produce the gene product encoded by the recombinant sequence. Alternatively, the proteins of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual, Second Edition*, Cold Spring Harbor, N.Y., (1989), the disclosure of which is hereby incorporated by reference.

Transcription of the DNA encoding the proteins of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, *Cell*, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The proteins according to the invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The proteins of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the proteins of the present invention may be glycosylated or may be non-glycosylated. Proteins of the invention may or may not also include an initial methionine amino acid residue.

Antibodies generated against a protein corresponding to a sequence of the present invention can be obtained by direct injection of the respective protein (or a portion of the protein) into an animal or by administering the proteins to an animal, preferably a nonhuman. The antibody so obtained will then bind the respective protein itself. In this manner, even a sequence encoding only a fragment of the proteins can be used to generate antibodies binding the whole native proteins. Such antibodies can then be used to isolate the protein from cells expressing that protein and may also be useful as antimicrobials, or controls in assays to determine the efficacy of potential antimicrobials.

For preparation of monoclonal antibodies, any technique which provides antibodies produced by continuous cell line cultures can be used. Examples include the hybridoma technique (Kohler and Milstein, *Nature,* 256:495–497, 1975), the trioma technique, the human B-cell hybridoma technique (Kozbor et al., *Immunology Today* 4:72, 1983), and the EBV-hybridoma technique to produce human monoclonal antibodies (Cole et al., in *Monoclonal Antibodies and Cancer Therapy*, Alan R. Liss, Inc., pp. 77–96, 1985).

Techniques described for the production of single chain antibodies (U.S. Pat. No. 4,946,778) can be adapted to produce single chain antibodies to immunogenic protein products of this invention. Also, transgenic mice may be used to express humanized antibodies to immunogenic protein products of this invention.

Antibodies generated against a protein of the present invention may be used in screening for similar proteins from other organisms and samples. Such screening techniques are known in the art, for example, one such screening assay is described in Sambrook and Maniatis, Molecular Cloning: A Laboratory Manual (2d Ed.), vol. 2:Section 8.49, Cold Spring Harbor Laboratory, 1989, which is hereby incorporated by reference in its entirety.

EXAMPLE 1
One-Step Gene Disruption

A mutation is constructed in vitro in a cloned gene and the gene having this mutation is reintroduced into the *Aspergillus fumigatus* wild type microbe. This allows assessment of genetic consequences of a mutation, and may be effectively used to determine whether or not a gene is essential (by determining if a complete gene deletion is viable on non-supplemented or limited supplemental media). The one-step gene disruption technique generates either insertion or deletion mutations.

A one-step gene disruption is generated in *Aspergillus fumigatus* in a single step via transformation, using a fragment of DNA containing a cloned gene that is disrupted by a selectable genetic marker (hygB), i.e., a hisB knock-out construct. A construct is made which corresponds to head and tail portions of the polynucleotide according to SEQ ID NO:1 wherein the center portion has been digested away with restriction enzymes and the marker gene hybB is sandwiched between the head and tail portions. For example, an hygB insert is used having the hygB gene flanked with BamHI and SaII restriction sites. After inverse digestion of the center portion of the polynucleotide sequence according to SEQ ID NO:1 of FIG. 1, the hygB insert is inserted to form the knock-out construct.

Homologous recombination is then carried out between the free DNA ends of the knock-out construct, which are highly recombinogenic, and homologous sequences in the *Aspergillus fumigatus* genome result in replacement of the wild-type gene by the disrupted copy (i.e., by the knock-out construct). In this illustration the disrupted gene has a portion deleted and a selectable marker inserted, however the disrupted gene can contain either a simple insertion (of the selectable marker) or a deletion/insertion mutation. Introduction of these disruptions into the genome can be achieved in a single step, resulting in stable, non-reverting mutations.

In the present example, the gene corresponding to SEQ ID NO:1 is mutated to result in a stable, essentially, non-reverting auxotroph of *Aspergillus fumitagus* that requires its growth medium to be supplemented with histidine or it its growth and reproduction are significantly affected. In fact, it will eventually die in an in vitro culture which is not supplemented with histidine. The steps utilized are as generally described as follows.

1. Subclone into gene of interest a suitable selectable gene, creating in the process of subcloning a deletion as well, if desired.

2. Using appropriate restriction sites, excise a linear fragment that contains disrupted gene from plasmid constructed in step 1 and gel purify. Transform with 1 to 10 μg of gel-purified fragment selecting for inserted marker.

Small amounts of vector sequences can be retained on this fragment without deleterious effects. Ideally, ≧250 bp of the cloned gene should bracket either side of inserted selectable gene, to promote recombination at the chromosomal locus of cloned gene, rather than at site of selectable marker.

3. Confirm structure of disruption by Southern hybridization.

The techniques of the above method are illustrated in FIG. 4. Pure colonies of potential transformant *Aspergillus fumigatus* species are obtained on fully supplemented media. Samples from each of such colonies are screened for histidine auxotrophic properties by utilizing a medium which is fully supplemented except that it lacks histidine. Failure to grow and reproduce on such media (slowed growth and reproduction) indicate a successful transformant histidine auxotroph. Of 175 colonies of potential transformants screened in a medium lacking the amino acid histidine, 20 transformant species were identified as auxotrophs of *Aspergillus fumigatus* that require histidine for growth.

Similarly, other auxotrophs lacking the polynucleotide sequence according to SEQ ID NO:1, or another important or essential gene (such as polynucleotides according to SEQ ID NO:2 or SEQ ID NO:3 are produced utilizing the above procedures.

EXAMPLE 2
Use of Histidine Auxotroph to Assay *Aspergillus fumigatus* cDNA libraries The histadine auxotroph (or another auxotroph) according to Example 1 above is utilized to screen a cDNA library for the function of such polynucleotide in *Aspergillus fumigatus*.

A cDNA library is formed from *Aspergillus fumigatus* and the cDNA clones are obtained. Preferably, after obtaining the sequence for the cDNA polynucleotide of a particular cDNA clone (for example having a polynucleotide sequence according to SEQ ID NO:2 of FIG. 2), a mutation of the cDNA is constructed in vitro and the gene having this mutation is reintroduced into the *Aspergillus fumigatus* histadine auxotroph. This allows assessment of genetic consequences of such mutation, and may be effectively used to determine whether or not a gene is essential (by determining if a complete gene deletion is viable on non-supplemented or limited supplemental media) and/or to determine its function. The one-step gene disruption technique generating either insertion or deletion mutations is preferred.

A one-step gene disruption is generated in *Aspergillus fumigatus* in a single step via transformation, using a fragment of DNA containing a cloned cDNA gene that is disrupted by a selectable genetic marker construct comprising the polynucleotide sequence according to SEQ ID NO:1), i.e., a cDNA knock-out construct. A construct is made which corresponds to head and tail portions of the polynucleotide as determined for the cDNA wherein the center portion has been digested away with restriction enzymes and the marker gene for histidine according to SEQ ID NO:1 is sandwiched between the head and tail portions. For example, an insert having the polynucleotide sequence according to SEQ ID NO:1 flanked with BamHI and SalI restriction sites. After inverse digestion of the center portion of the polynucleotide sequence of the cDNA, the insert comprising the polynucleotide sequence according to SEQ ID NO:1 is inserted to form the knock-out construct against the cDNA of interest.

Homologous recombination is then carried out between the free DNA ends of the knock-out construct, which are highly recombinogenic, and homologous sequences in the *Aspergillus fumigatus* genome result in replacement of the wild-type gene by the disrupted copy (i.e., by the knock-out construct). In this illustration the disrupted gene has a portion deleted and a selectable marker inserted, however the disrupted gene can contain either a simple insertion (of the selectable marker) or a deletion/insertion mutation. Introduction of these disruptions into the genome can be achieved in a single step, resulting in stable, non-reverting mutations.

In the present example, the gene corresponding to the cDNA of interest is mutated to result in a removal of the histidine auxotrophic characteristics of *Aspergillus fumitagus* in that it no longer requires its growth medium to be supplemented with histidine to prevent its growth and reproduction are significantly affected.

Successful transformations are efficiently screened with a media that is fully supplement except that it lacks the amino acid histadine. Species that survive on such media indicate that successful cross-over has occurred and that the cDNA gene has been placed by the knock-out construct that reverses the requirement for histidine supplemented media. Pure colonies of the transformants are obtained of supplemented media and then screened further for other lost properties.

Advantageously, multiple screening plates are utilized from which a single nutrient or factor has been removed. Slowed growth and reproduction or cell death on a media lacking a certain nutrient or factor indicates the function of the cDNA clone polynucleotide. In the instant illustration when the transformants are screened on a media lacking adenylic acid, cell death occurs. Therefore, the polynucleotide according to SEQ ID NO:2 of FIG. 2 encodes a protein critical to the production of adenylic acid in *Aspergillus fumigatus*. Similarly, other cDNA clones from *Aspergillus fumigatus* may be screen for their function with this organism.

As shown by the above example, inter alia the auxotrophs according to the present invention are useful to study cDNA libraries of *Aspergillus fumigatus*.

Numerous modifications and variations of the present invention are possible in light of the above teachings and, therefore, within the scope of the appended claims, the invention may be practiced otherwise than as particularly described.

What is claimed is:

1. An isolated polynucleotide comprising a polynucleotide having at least 95% identity to a member selected from the group consisting of:

(a) a polynucleotide encoding a polypeptide comprising amino acids 2 to 244 of SEQ ID NO:2;

(b) a polynucleotide encoding a polypeptide comprising amino acids 2 to 572 of SEQ ID NO:4;

(c) a polynucleotide encoding a polypeptide comprising amino acids 2 to 366 of SEQ ID NO:6; and (d) the complement of (a), (b) or (c).

2. The isolated polynucleotide of claim 1 wherein said member is (a) and said member has the polynucleotide sequence of SEQ ID NO:1.

3. The isolated polynucleotide of claim 1 wherein said member is (b) and said member has the polynucleotide sequence of SEQ ID NO:3.

4. The isolated polynucleotide of claim 1 wherein said member is (c) and said member has the polynucleotide sequence of SEQ ID NO:5.

5. A recombinant vector comprising the polynucleotide of claim 1, wherein said polynucleotide is DNA.

6. A recombinant host cell comprising the polynucleotide of claim 1, wherein said polynucleotide is DNA.

7. A method for producing a polypeptide comprising expressing from the recombinant cell of claim 6 the polypeptide encoded by said polynucleotide.

8. An isolated polynucleotide comprising a polynucleotide sequence having at least 95% identity to the polynucleotide sequence of a member selected from the group consisting of SEQ ID NOS: 1, 3, and 5, and the complements of SEQ ID NOS: 1, 3, and 5.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 732 BASE PAIRS
      (B) TYPE: NUCLEIC ACID
      (C) STRANDEDNESS: SINGLE
      (D) TOPOLOGY: LINEAR (ii) MOLECULE TYPE: cDNA (xi) SEQUENCE DESCRIPTION: SEQ ID NO:1:

```
ATG TCT CTC CCC GCA CGA ACA GCG ACC GTC TCG CGG GTG ACC AAC            45
Met Ser Leu Pro Ala Arg Thr Ala Thr Val Ser Arg Val Thr Asn
              5                  10                  15

GAG ACC AAG ATC CAG GTG TCT CTC TCT CTC GAC GGC GGC GTC CTC            90
Glu Thr Lys Ile Gln Val Ser Leu Ser Leu Asp Gly Gly Val Leu
             20                  25                  30

CCT CCA TAT GAG CCG TCA GAT CAT TTC CCT GCT CCT GAA GAC CCG           135
Pro Pro Tyr Glu Pro Ser Asp His Phe Pro Ala Pro Glu Asp Pro
             35                  40                  45

AAG GAG GCA GAG GCC GCC AAG CAT GGC ATC GTC CCC CCC AAA AAT           180
Lys Glu Ala Glu Ala Ala Lys His Gly Ile Val Pro Pro Lys Asn
             50                  55                  60

GCC GCC CAT GCG ACC CAG TTC ACA CCG ACC CAG CAG ATC ACC GTA           225
Ala Ala His Ala Thr Gln Phe Thr Pro Thr Gln Gln Ile Thr Val
             65                  70                  75

AGC ACG GGG ATC GGA TTT CTG GAT CAC ATG CTG CAT GCT CTC GCC           270
Ser Thr Gly Ile Gly Phe Leu Asp His Met Leu His Ala Leu Ala
             80                  85                  90
```

```
AAA CAC TCT GGG TGG AGT TTA GCC ATC AGA GCC AAG GGA GAT CTG              315
Lys His Ser Gly Trp Ser Leu Ala Ile Arg Ala Lys Gly Asp Leu
             95                 100                 105

TAC ATT GAC GAC CAC CAC ACC ACC GAA GAT ACC TTC CTT GCG CTC              360
Tyr Ile Asp Asp His His Thr thr Glu Asp Thr Phe Leu Ala Leu
            110                 115                 120

GGT ACC GCC TTT ACC AAA GCT CTA GGC GCC CGG CAA TCT CTT GCA              405
Gly Thr Ala Phe Thr Lys Ala Leu Gly Ala Arg Gln Ser Leu Ala
            125                 130                 135

CGA TTT GGA CGC GGC GAC GCT CCA CTC GAC GAG GCT CTC TCC TGG              450
Arg Phe Gly Arg Gly Asp Ala Pro Leu Asp Glu Ala Leu Ser Trp
            140                 145                 150

GCT GTG ATC GAC CTC TCC AGC CGT CCC TGG GCC GTG ATC AAC CTG              495
Ala Val Ile Asp Leu Ser Ser Arg Pro Trp Ala Val Ile Asn Leu
            155                 160                 165

GGC TTC AAG CGG GAG AAG ATC GGA GAC CTG AGC ACC GAG ATG ATC              540
Gly Phe Lys Arg Glu Lys Ile Gly Asp Leu Ser Thr Glu Met Ile
            170                 175                 180

ACT CAT GGA CTG CAC AGC TTC GCG CAG GCT GCC GAT GTA ACG CTG              585
Thr His Gly Leu His Ser Phe Ala Gln Ala Ala Asp Val Thr Leu
            185                 190                 195

CAT GTT GGC TGC ACA TAC GGA GAT AAC GAC CAC CAC CGT GCA GAG              630
His Val Gly Cys Thr Tyr Gly Asp Asn Asp His His Arg Ala Glu
            200                 205                 210

AGT GCG TTC AAG GCG CTG GCC GTA GCT ATC CGC ACT GCC TGT ACC              675
Ser Ala Phe Lys Ala Leu Ala Val Ala Ile Arg Thr Ala Cys Thr
            215                 220                 225

AGA AGG GTG GCT GGC GAA GTT GGA GCG GGA GAT GTG GTT AGT ACA              720
Arg Arg Val Ala Gly Glu Val Gly Ala Gly Asp Val Val Ser Thr
            230                 235                 240

AAG GGA GTG CTG                                                          732
Lys Gly Val Leu (2) INFORMATION FOR SEQ ID NO:2:

(i) SEQUENCE CHARACTERISTICS:
        (A) LENGTH:  244 AMINO ACIDS
        (B) TYPE:  AMINO ACID
        (C) STRANDEDNESS:
        (D) TOPOLOGY:  LINEAR (ii) MOLECULE TYPE:  PROTEIN (xi) SEQUENCE DESCRIPTION:  SEQ ID NO:2:

Met Ser Leu Pro Ala Arg Thr Ala Thr Val Ser Arg Val Thr Asn
              5                  10                  15

Glu Thr Lys Ile Gln Val Ser Leu Ser Leu Asp Gly Gly Val Leu
             20                  25                  30

Pro Pro Tyr Glu Pro Ser Asp His Phe Pro Ala Pro Glu Asp Pro
             35                  40                  45

Lys Glu Ala Glu Ala Ala Lys His Gly Ile Val Pro Pro Lys Asn
             50                  55                  60

Ala Ala His Ala Thr Gln Phe Thr Pro Thr Gln Gln Ile Thr Val
             65                  70                  75

Ser Thr Gly Ile Gly Phe Leu Asp His Met Leu His Ala Leu Ala
             80                  85                  90

Lys His Ser Gly Trp Ser Leu Ala Ile Arg Ala Lys Gly Asp Leu
             95                 100                 105

Tyr Ile Asp Asp His His Thr thr Glu Asp Thr Phe Leu Ala Leu
            110                 115                 120
```

```
Gly Thr Ala Phe Thr Lys Ala Leu Gly Ala Arg Gln Ser Leu Ala
            125                 130                 135

Arg Phe Gly Arg Gly Asp Ala Pro Leu Asp Glu Ala Leu Ser Trp
            140                 145                 150

Ala Val Ile Asp Leu Ser Ser Arg Pro Trp Ala Val Ile Asn Leu
            155                 160                 165

Gly Phe Lys Arg Glu Lys Ile Gly Asp Leu Ser Thr Glu Met Ile
            170                 175                 180

Thr His Gly Leu His Ser Phe Ala Gln Ala Ala Asp Val Thr Leu
            185                 190                 195

His Val Gly Cys Thr Tyr Gly Asp Asn Asp His His Arg Ala Glu
            200                 205                 210

Ser Ala Phe Lys Ala Leu Ala Val Ala Ile Arg Thr Ala Cys Thr
            215                 220                 225

Arg Arg Val Ala Gly Glu Val Gly Ala Gly Asp Val Val Ser Thr
            230                 235                 240

Lys Gly Val Leu (2) INFORMATION FOR SEQ ID NO:3:

(i) SEQUENCE CHARACTERISTICS:
        (A) LENGTH: 1716 BASE PAIRS
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:3:

ATG TGG AAC TCT CCA AAG GTG GGG GTC CTC GGT GGA GGT CAG TTG                45
Met Trp Asn Ser Pro Lys Val Gly Val Leu Gly Gly Gly Gln Leu
              5                  10                  15

GGA CGA ATG CTT GTT GAG TCG GCG AAC CGA CTT AAT ATC CAG GTC                90
Gly Arg Met Leu Val Glu Ser Ala Asn Arg Leu Asn Ile Gln Val
             20                  25                  30

AAT GTT CTG GAC GCC GGT AAC GCC CCT GCG AAA CAA ATT AGC GCC               135
Asn Val Leu Asp Ala Gly Asn Ala Pro Ala Lys Gln Ile Ser Ala
         35                  40                  45

CAC GAC GGC CAT GTG ACT GGC TCA TTC AAG GAT CGT GAA GCT GTG               180
His Asp Gly His Val Thr Gly Ser Phe Lys Asp Arg Glu Ala Val
         50                  55                  60

CGG ACG TTG GCG AGG ACC TGC GAC GTT GTG ACG GCC GAG ATC GAG               225
Arg Thr Leu Ala Arg Thr Cys Asp Val Val Thr Ala Glu Ile Glu
         65                  70                  75

CAT GTT GAT ACA TAC GCT CTT GAG GAG ATC TCC GCG GAG GTC AAG               270
His Val Asp Thr Tyr Ala Leu Glu Glu Ile Ser Ala Glu Val Lys
         80                  85                  90

GTT GAG CCC AGC TGG CAA GCG ATC CGA ACA ATC CAG AAC AAG TTC               315
Val Glu Pro Ser Trp Gln Ala Ile Arg Thr Ile Gln Asn Lys Phe
         95                 100                 105

AAT CAG AAG GAA CAC CTT CGG AAA TAT GGC ATA CCA ATG GCG GAG               360
Asn Gln Lys Glu His Leu Arg Lys Tyr Gly Ile Pro Met Ala Glu
        110                 115                 120

CAC CGG GAG CTG CTT GAG AAC ACG CCG GCT GAA CTC GCC CAG ATC               405
His Arg Glu Leu Leu Glu Asn Thr Pro Ala Glu Leu Ala Gln Ile
        125                 130                 135

GGC GAA CAG CTT GGG TAT CCC TTG ATG CTC AAG TCG AAG ACG ATG               450
Gly Glu Gln Leu Gly Tyr Pro Leu Met Leu Lys Ser Lys Thr Met
        140                 145                 150
```

```
GCC TAC GAC GGA CGG GGA AAC TTC CGT GTC AAT TCC AAG GAC GAT         495
Ala Tyr Asp Gly Arg Gly Asn Phe Arg Val Asn Ser Lys Asp Asp
                155                 160                 165

ATC CCC GAA GCG CTT GAA GCG CTC AAG GAC CGG CCA TTG TAC GCT         540
Ile Pro Glu Ala Leu Glu Ala Leu Lys Asp Arg Pro Leu Tyr Ala
                170                 175                 180

GAG AAA TGG GCC TAC TTC AAG ATG GAA TTG GCC GTA ATG GTT GTG         585
Glu Lys Trp Ala Tyr Phe Lys Met Glu Leu Ala Val Met Val Val
                185                 190                 195

AAA ACC AAG GAC GCG GTC CTC TCA TAC CCC ACA GTC GAG ACA GTA         630
Lys Thr Lys Asp Ala Val Leu Ser Tyr Pro Thr Val Glu Thr Val
                200                 205                 210

CAA GAA GAT TCG ATA TGC AAG CTC GTC TAC GCA CCT GCC CGC AAT         675
Gln Glu Asp Ser Ile Cys Lys Leu Val Tyr Ala Pro Ala Arg Asn
                215                 220                 225

GTC TCC GAC GCC ATC AAC CAG AAA GCC CAG GAG CTA GCC CGC AAG         720
Val Ser Asp Ala Ile Asn Gln Lys Ala Gln Glu Leu Ala Arg Lys
                230                 235                 240

GCT GTC GCA GCC TTT GAC GGC AAG GGT GCT TTC GGT GTG GAG ATG         765
Ala Val Ala Ala Phe Asp Gly Lys Gly Ala Phe Gly Val Glu Met
                245                 250                 255

TTC CTT CTC GAG GAC GAC AGC ATC ATG CTG TGC GAA ATT GCC AGC         810
Phe Leu Leu Glu Asp Asp Ser Ile Met Leu Cys Glu Ile Ala Ser
                260                 265                 270

CGC ATC CAC AAC TCG GGC CAC TAC ACA ATT GAA GGT TGT ACC CTG         855
Arg Ile His Asn Ser Gly His Tyr Thr Ile Glu Gly Cys Thr Leu
                275                 280                 285

TCC CAA TTT GAC GCC CAC CTA CGT GCC ATT CTC GAC CTC CCC ATT         900
Ser Gln Phe Asp Ala His Leu Arg Ala Ile Leu Asp Leu Pro Ile
                290                 295                 300

CCC CCT CAG AGC CTC GAA ATC CGC CAA CCG TCC ATC ATG CTC AAC         945
Pro Pro Gln Ser Leu Glu Ile Arg Gln Pro Ser Ile Met Leu Asn
                305                 310                 315

ATC ATT GGC GGC GCC GCC CCA GAC ACC CAC CTG AAA GCC GCC GAG         990
Ile Ile Gly Gly Ala Ala Pro Asp Thr His Leu Lys Ala Ala Glu
                320                 325                 330

GCC GCT CTC TCC ATC CCC AAC GCC AGC ATT CAC CTC TAC AGC AAG        1035
Ala Ala Leu Ser Ile Pro Asn Ala Ser Ile His Leu Tyr Ser Lys
                335                 340                 345

GGC GCC GCC AAG CCC GGC CGC AAG ATG GGC CAC GTC ACC GTT ACC        1080
Gly Ala Ala Lys Pro Gly Arg Lys Met Gly His Val Thr Val Thr
                350                 355                 360

GCG TCC ACG ATG CAC GAA GCC GAG AAA TAC ATC CAG CCC CTG ATC        1125
Ala Ser Thr Met His Glu Ala Glu Lys Tyr Ile Gln Pro Leu Ile
                365                 370                 375

GAC GTT GTT GAC GAG ATC CGC TCG AAG CGC AGC GAC ATC AAG ACA        1170
Asp Val Val Asp Glu Ile Arg Ser Lys Arg Ser Asp Ile Lys Thr
                380                 385                 390

CAG CCC GTC AAG TCC GGC CCG TCG AAG CCC GCC CCC ACC GTT GCT        1215
Gln Pro Val Lys Ser Gly Pro Ser Lys Pro Ala Pro Thr Val Ala
                395                 400                 405

GTG ATG ATG GGC TCC GAT AGC GAC CTC AAG ACA CTC GTT CCG GGC        1260
Val Met Met Gly Ser Asp Ser Asp Leu Lys Thr Leu Val Pro Gly
                410                 415                 420

CTG AAA CTC CTC CGT GAC TAC TTC GGC ATC GAG CCC GCC GTC GAC        1305
Leu Lys Leu Leu Arg Asp Tyr Phe Gly Ile Glu Pro Ala Val Asp
                425                 430                 435

ATC ACC TCC GCC CAT CGC ACC CCA ACG TTC ATG GCC GAG TAC TCA        1350
Ile Thr Ser Ala His Arg Thr Pro Thr Phe Met Ala Glu Tyr Ser
```

-continued

```
                     440                 445                 450
GCC AGC GCA GCC GCG CGC GGC ATT AAG GTC ATT ATC GCC GCT GCG          1395
Ala Ser Ala Ala Ala Arg Gly Ile Lys Val Ile Ile Ala Ala Ala
                     455                 460                 465

GGC GGC GCC GCC CAT CTC CCT GGG ATG GCT GCC GCA CAC ACC GTC          1440
Gly Gly Ala Ala His Leu Pro Gly Met Ala Ala Ala His Thr Val
                     470                 475                 480

CTG CCC GTC ATC GGC GTA CCG GTC AAG GGC AGC TCG CTA GAC GGC          1485
Leu Pro Val Ile Gly Val Pro Val Lys Gly Ser Ser Leu Asp Gly
                     485                 490                 495

GTG GAC AGC CTG TAC AGC ATC GTC CAG ATG CCT AGA GGT GTT CCC          1530
Val Asp Ser Leu Tyr Ser Ile Val Gln Met Pro Arg Gly Val Pro
                     500                 505                 510

GTC GCG ACG GTA GGA ATC AAC AAC AGC ATC AAC GCT GCC CTC CTG          1575
Val Ala Thr Val Gly Ile Asn Asn Ser Ile Asn Ala Ala Leu Leu
                     515                 520                 525

GCA GCT CGT ATC CTT GGC ACA TTC GAC CCG GCT ATC CAG CGT AAG          1620
Ala Ala Arg Ile Leu Gly Thr Phe Asp Pro Ala Ile Gln Arg Lys
                     530                 535                 540

GTG GAG GCG TAT GCC GAG CAG GCT AGA CAC GAG AAC ATG GAG TTG          1665
Val Glu Ala Tyr Ala Glu Gln Ala Arg His Glu Asn Met Glu Leu
                     545                 550                 555

AAG GGG ACC AAG ATG CAG GAA CTC GGA TGG GAA AAG TAC TTT GAA          1710
Lys Gly Thr Lys Met Gln Glu Leu Gly Trp Glu Lys Tyr Phe Glu
                     560                 565                 570

CAG ATG                                                              1716
Gln Met
```

(2) INFORMATION FOR SEQ ID NO:4:

(i) SEQUENCE CHARACTERISTICS:
        (A) LENGTH: 572 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:4:

```
Met Trp Asn Ser Pro Lys Val Gly Val Leu Gly Gly Gly Gln Leu
                  5                  10                  15

Gly Arg Met Leu Val Glu Ser Ala Asn Arg Leu Asn Ile Gln Val
                 20                  25                  30

Asn Val Leu Asp Ala Gly Asn Ala Pro Ala Lys Gln Ile Ser Ala
                 35                  40                  45

His Asp Gly His Val Thr Gly Ser Phe Lys Asp Arg Glu Ala Val
                 50                  55                  60

Arg Thr Leu Ala Arg Thr Cys Asp Val Val Thr Ala Glu Ile Glu
                 65                  70                  75

His Val Asp Thr Tyr Ala Leu Glu Glu Ile Ser Ala Glu Val Lys
                 80                  85                  90

Val Glu Pro Ser Trp Gln Ala Ile Arg Thr Ile Gln Asn Lys Phe
                 95                 100                 105

Asn Gln Lys Glu His Leu Arg Lys Tyr Gly Ile Pro Met Ala Glu
                110                 115                 120

His Arg Glu Leu Leu Glu Asn Thr Pro Ala Glu Leu Ala Gln Ile
                125                 130                 135

Gly Glu Gln Leu Gly Tyr Pro Leu Met Leu Lys Ser Lys Thr Met
                140                 145                 150
```

```
Ala Tyr Asp Gly Arg Gly Asn Phe Arg Val Asn Ser Lys Asp Asp
            155                 160                 165
Ile Pro Glu Ala Leu Glu Ala Leu Lys Asp Arg Pro Leu Tyr Ala
            170                 175                 180
Glu Lys Trp Ala Tyr Phe Lys Met Glu Leu Ala Val Met Val Val
            185                 190                 195
Lys Thr Lys Asp Ala Val Leu Ser Tyr Pro Thr Val Glu Thr Val
            200                 205                 210
Gln Glu Asp Ser Ile Cys Lys Leu Val Tyr Ala Pro Ala Arg Asn
            215                 220                 225
Val Ser Asp Ala Ile Asn Gln Lys Ala Gln Glu Leu Ala Arg Lys
            230                 235                 240
Ala Val Ala Ala Phe Asp Gly Lys Gly Ala Phe Gly Val Glu Met
            245                 250                 255
Phe Leu Leu Glu Asp Asp Ser Ile Met Leu Cys Glu Ile Ala Ser
            260                 265                 270
Arg Ile His Asn Ser Gly His Tyr Thr Ile Glu Gly Cys Thr Leu
            275                 280                 285
Ser Gln Phe Asp Ala His Leu Arg Ala Ile Leu Asp Leu Pro Ile
            290                 295                 300
Pro Pro Gln Ser Leu Glu Ile Arg Gln Pro Ser Ile Met Leu Asn
            305                 310                 315
Ile Ile Gly Gly Ala Ala Pro Asp Thr His Leu Lys Ala Ala Glu
            320                 325                 330
Ala Ala Leu Ser Ile Pro Asn Ala Ser Ile His Leu Tyr Ser Lys
            335                 340                 345
Gly Ala Ala Lys Pro Gly Arg Lys Met Gly His Val Thr Val Thr
            350                 355                 360
Ala Ser Thr Met His Glu Ala Glu Lys Tyr Ile Gln Pro Leu Ile
            365                 370                 375
Asp Val Val Asp Glu Ile Arg Ser Lys Arg Ser Asp Ile Lys Thr
            380                 385                 390
Gln Pro Val Lys Ser Gly Pro Ser Lys Pro Ala Pro Thr Val Ala
            395                 400                 405
Val Met Met Gly Ser Asp Ser Asp Leu Lys Thr Leu Val Pro Gly
            410                 415                 420
Leu Lys Leu Leu Arg Asp Tyr Phe Gly Ile Glu Pro Ala Val Asp
            425                 430                 435
Ile Thr Ser Ala His Arg Thr Pro Thr Phe Met Ala Glu Tyr Ser
            440                 445                 450
Ala Ser Ala Ala Ala Arg Gly Ile Lys Val Ile Ile Ala Ala Ala
            455                 460                 465
Gly Gly Ala Ala His Leu Pro Gly Met Ala Ala His Thr Val
            470                 475                 480
Leu Pro Val Ile Gly Val Pro Val Lys Gly Ser Ser Leu Asp Gly
            485                 490                 495
Val Asp Ser Leu Tyr Ser Ile Val Gln Met Pro Arg Gly Val Pro
            500                 505                 510
Val Ala Thr Val Gly Ile Asn Asn Ser Ile Asn Ala Ala Leu Leu
            515                 520                 525
Ala Ala Arg Ile Leu Gly Thr Phe Asp Pro Ala Ile Gln Arg Lys
            530                 535                 540
```

```
Val Glu Ala Tyr Ala Glu Gln Ala Arg His Glu Asn Met Glu Leu
            545                 550                 555

Lys Gly Thr Lys Met Gln Glu Leu Gly Trp Glu Lys Tyr Phe Glu
            560                 565                 570

Gln Met (2) INFORMATION FOR SEQ ID NO:5:

(i) SEQUENCE CHARACTERISTICS:
        (A) LENGTH:  1098 BASE PAIRS
        (B) TYPE:  NUCLEIC ACID
        (C) STRANDEDNESS:  SINGLE
        (D) TOPOLOGY:  LINEAR (ii) MOLECULE TYPE:  cDNA (xi) SEQUENCE DESCRIPTION:  SEQ ID NO:5:

ATG CCG TCA TAT AAC ATT GTC GTT TTC GCT GGG GAC CAC TGT GGT            45
Met Pro Ser Tyr Asn Ile Val Val Phe Ala Gly Asp His Cys Gly
              5                  10                  15

CCG GAG GTG ACC GCT GAG GCA ATC AAG GTC CTG CGC GTC ATC GAG            90
Pro Glu Val Thr Ala Glu Ala Ile Lys Val Leu Arg Val Ile Glu
             20                  25                  30

AAG TGC CGT GAC GAT GCT ACC TTC AAC CTC CAG GAT CAA TTG CTC           135
Lys Cys Arg Asp Asp Ala Thr Phe Asn Leu Gln Asp Gln Leu Leu
         35                  40                  45

GGT GGT GCA TCG ATC GAT GCT ACC GGA TCT CCC CTT ACC GAC GAA           180
Gly Gly Ala Ser Ile Asp Ala Thr Gly Ser Pro Leu Thr Asp Glu
         50                  55                  60

GCT CTT AAC GCC GCA AAG AAC GCC GAT GCC GTT CTC CTC GGT GCC           225
Ala Leu Asn Ala Ala Lys Asn Ala Asp Ala Val Leu Leu Gly Ala
         65                  70                  75

ATT GGC GGT CCC AAA TGG GGC ACT GGC GCC GTC CGC CCC GAA CAG           270
Ile Gly Gly Pro Lys Trp Gly Thr Gly Ala Val Arg Pro Glu Gln
         80                  85                  90

GGC CTC CTC CGT CTG CGC AAG GAG ATG GGC ACA TTC GGT AAC CTC           315
Gly Leu Leu Arg Leu Arg Lys Glu Met Gly Thr Phe Gly Asn Leu
         95                 100                 105

CGC CCC TGC AAC TTC GCC GCC CCG TCG CTG GTC GAC GGC TCC CCT           360
Arg Pro Cys Asn Phe Ala Ala Pro Ser Leu Val Asp Gly Ser Pro
        110                 115                 120

CTC CGC CCC GAA GTC TGC CGC GGC GTC GAC TTC AAC ATT ATC CGC           405
Leu Arg Pro Glu Val Cys Arg Gly Val Asp Phe Asn Ile Ile Arg
        125                 130                 135

GAA CTG ACC GGT GGC ATC TAC TTC GGC GAC CGC AAG GAG GAC GAC           450
Glu Leu Thr Gly Gly Ile Tye Phe Gly Asp Arg Lys Glu Asp Asp
        140                 145                 150

GGC AGC GGC TTC GCC ATG GAC ACG GAG CCG TAC TCC CGC GCG GAG           495
Gly Ser Gly Phe Ala Met Asp Thr Glu Pro Tyr Ser Arg Ala Glu
        155                 160                 165

ATC GAG CGC ATC ACC CGC CTT GCG GCC CAC CTC GCT CTG CAG CAC           540
Ile Glu Arg Ile Thr Arg Leu Ala Ala His Leu Ala Leu Gln His
        170                 175                 180

AAC CCC CCT CTT CCC GTG TGG AGC TTG GAC AAG GCC AAC GTC CTC           585
Asn Pro Pro Leu Pro Val Trp Ser Leu Asp Lys Ala Asn Val Leu
        185                 190                 195

GCG ACG AGC CGG CTG TGG CGG AAG ACC GTG ACG GAG GTC ATG GCC           630
Ala Thr Ser Arg Leu Trp Arg Lys Thr Val Thr Glu Val Met Ala
        200                 205                 210

AAG GAG TTC CCC CAG CTC AAG GTG GAG CAC CAG CTC ATT GAC TCC           675
Lys Glu Phe Pro Gln Leu Lys Val Glu His Gln Leu Ile Asp Ser
```

```
                         215                 220                 225
GCG GCC ATG ATC ATG GTC AAG GAG CCT AGA AAG CTT AAC GGT ATT         720
Ala Ala Met Ile Met Val Lys Glu Pro Arg Lys Leu Asn Gly Ile
                    230                 235                 240

GTT GTC ACT AGC AAC CTG TTC GGT GAC ATC ATC AGT GAT GAA GCC         765
Val Val Thr Ser Asn Leu Phe Gly Asp Ile Ile Ser Asp Glu Ala
                    245                 250                 255

AGC GTT ATC CCT GGT TCT CTG GGA CTC TTG CCC AGC GCA AGC TTG         810
Ser Val Ile Pro Gly Ser Leu Gly Leu Leu Pro Ser Ala Ser Leu
                    260                 265                 270

AGC GGC ATT CCT GAC GGA AAG ACC AAG GTC AAT GGT ATC TAT GAG         855
Ser Gly Ile Pro Asp Gly Lys Thr Lys Val Asn Gly Ile Tyr Glu
                    275                 280                 285

CCT ATT CAC GGT TCT GCC CCT GAC ATT GCC GGC AAG GGC ATC GTT         900
Pro Ile His Gly Ser Ala Pro Asp Ile Ala Gly Lys Gly Ile Val
                    290                 295                 300

AAC CCC GTC GCC GCC ATT CTC TCT GTC GCC ATG ATG ATG CAG TAC         945
Asn Pro Val Ala Ala Ile Leu Ser Val Ala Met Met Met Gln Tyr
                    305                 310                 315

TCC CTG AAC CGT ATG GAT GAC GCC AGG GCC ATC GAG ACG GCC GTC         990
Ser Leu Asn Arg Met Asp Asp Ala Arg Ala Ile Glu Thr Ala Val
                    320                 325                 330

CGC AAT GTG ATC GAG GCC GGT ATC CGC ACT GCC GAT ATT GGC GGC        1035
Arg Asn Val Ile Glu Ala Gly Ile Arg Thr Ala Asp Ile Gly Gly
                    335                 340                 345

AAG TCG ACA ACT AGC GAG GTC GGT GAC GCT GTT GCT GCC GAG CTG        1080
Lys Ser Thr Thr Ser Glu Val Gly Asp Ala Val Ala Ala Glu Leu
                    350                 355                 360

GAG AAG CTG TTG AAG CAA                                            1098
Glu Lys Leu Leu Lys Gln
                    365

(2) INFORMATION FOR SEQ ID NO:6:

(i) SEQUENCE CHARACTERISTICS:
        (A) LENGTH:  366 AMINO ACIDS
        (B) TYPE:  AMINO ACID
        (C) STRANDEDNESS:
        (D) TOPOLOGY:  LINEAR (ii) MOLECULE TYPE:  PROTEIN (xi) SEQUENCE DESCRIPTION:  SEQ ID NO:6:

Met Pro Ser Tyr Asn Ile Val Val Phe Ala Gly Asp His Cys Gly
                 5                  10                  15

Pro Glu Val Thr Ala Glu Ala Ile Lys Val Leu Arg Val Ile Glu
                20                  25                  30

Lys Cys Arg Asp Asp Ala Thr Phe Asn Leu Gln Asp Gln Leu Leu
                35                  40                  45

Gly Gly Ala Ser Ile Asp Ala Thr Gly Ser Pro Leu Thr Asp Glu
                50                  55                  60

Ala Leu Asn Ala Ala Lys Asn Ala Asp Ala Val Leu Leu Gly Ala
                65                  70                  75

Ile Gly Gly Pro Lys Trp Gly Thr Gly Ala Val Arg Pro Glu Gln
                80                  85                  90

Gly Leu Leu Arg Leu Arg Lys Glu Met Gly Thr Gly Phe Gly Asn Leu
                95                 100                 105

Arg Pro Cys Asn Phe Ala Ala Pro Ser Leu Val Asp Gly Ser Pro
               110                 115                 120
```

```
-continued

Leu Arg Pro Glu Val Cys Arg Gly Val Asp Phe Asn Ile Ile Arg
                125                 130             135

Glu Leu Thr Gly Gly Ile Tyr Phe Gly Asp Arg Lys Glu Asp Asp
                140                 145             150

Gly Ser Gly Phe Ala Met Asp Thr Glu Pro Tyr Ser Arg Ala Glu
                155                 160             165

Ile Glu Arg Ile Thr Arg Leu Ala Ala His Leu Ala Leu Gln His
                170                 175             180

Asn Pro Pro Leu Pro Val Trp Ser Leu Asp Lys Ala Asn Val Leu
                185                 190             195

Ala Thr Ser Arg Leu Trp Arg Lys Thr Val Thr Glu Val Met Ala
                200                 205             210

Lys Glu Phe Pro Gln Leu Lys Val Glu His Gln Leu Ile Asp Ser
                215                 220             225

Ala Ala Met Ile Met Val Lys Glu Pro Arg Lys Leu Asn Gly Ile
                230                 235             240

Val Val Thr Ser Asn Leu Phe Gly Asp Ile Ile Ser Asp Glu Ala
                245                 250             255

Ser Val Ile Pro Gly Ser Leu Gly Leu Leu Pro Ser Ala Ser Leu
                260                 265             270

Ser Gly Ile Pro Asp Gly Lys Thr Lys Val Asn Gly Ile Tyr Glu
                275                 280             285

Pro Ile His Gly Ser Ala Pro Asp Ile Ala Gly Lys Gly Ile Val
                290                 295             300

Asn Pro Val Ala Ala Ile Leu Ser Val Ala Met Met Met Gln Tyr
                305                 310             315

Ser Leu Asn Arg Met Asp Asp Ala Arg Ala Ile Glu Thr Ala Val
                320                 325             330

Arg Asn Val Ile Glu Ala Gly Ile Arg Thr Ala Asp Ile Gly Gly
                335                 340             345

Lys Ser Thr Thr Ser Glu Val Gly Asp Ala Val Ala Ala Glu Leu
                350                 355             360

Glu Lys Leu Leu Lys Gln
                365
```